United States Patent [19]

Schacht et al.

[11] 4,289,774
[45] Sep. 15, 1981

[54] LIPID LOWERING AND ANTI-THROMBOTIC 6-ARYLPYRIDAZIN-3-ONES AND A PROCESS FOR THEIR PREPARATION

[75] Inventors: Erich Schacht, Seeheim; Hans-Adolf Kurmeier, Darmstadt; Joachim Gante, Darmstadt-Arheilgen; Reinhard Lissner, Fischbachtal-Lichtenberg; Guido Melzer, Hofheim; Dieter Orth, Darmstadt, all of Fed. Rep. of Germany

[73] Assignee: Merck Patent Gesellschaft mit beschränkter Haftung, Darmstadt, Fed. Rep. of Germany

[21] Appl. No.: 86,604

[22] Filed: Oct. 19, 1979

[30] Foreign Application Priority Data

Oct. 19, 1978 [DE] Fed. Rep. of Germany ....... 2845456

[51] Int. Cl.³ .............. C07D 237/04; A61K 31/50; C07D 237/26; C07D 401/04
[52] U.S. Cl. .................. 424/250; 544/237; 544/238; 544/239
[58] Field of Search .............. 544/239, 237, 238; 424/250

[56] References Cited

U.S. PATENT DOCUMENTS

| | | | |
|---|---|---|---|
| 3,682,914 | 8/1972 | Tamamoto | 544/239 |
| 3,689,652 | 9/1972 | Curran | 544/239 |
| 3,812,256 | 5/1974 | Curran | 544/239 |
| 3,822,260 | 7/1974 | Curran | 544/239 |
| 3,931,177 | 1/1976 | Coates | 544/239 |
| 4,088,762 | 5/1978 | Hakim | 544/239 |

FOREIGN PATENT DOCUMENTS 2435244 5/1976 Fed. Rep. of Germany .

OTHER PUBLICATIONS

Fateen et al., J. Chem. U.A.R. 10, 321 (1967).
Fateen et al., Chem. Abs. 70, 3997m (1967).
Kulkarni, Current Science 46, 801-3 (1977).
Curran IV, J. Med. Chem. 17, 273 (1974).
Pitarch et al., European J. Med. Chem. 9, 644 (1974).
Child et al., J. Pharm Sci 66, 466 (1977).

Primary Examiner—Mark L. Berch
Attorney, Agent, or Firm—Millen & White

[57] ABSTRACT

Compounds of the formula

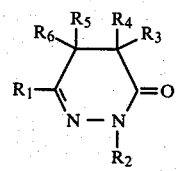

wherein $R^1$ is 4-biphenylyl, 4-phenoxyphenyl or 4-biphenylyl or 4-phenoxyphenyl substituted in the 4'-position by F, Cl, Br or I; $R^2$ is H, $C_{1-4}$-alkyl, hydroxy-$C_{1-4}$-alkyl or pyridyl; $R^3$ and $R^6$ are each H or alkyl of 1-4 carbon atoms, or together are —$(CH_2)_4$—; and $R^4$ and $R^5$ are each H or together are a C—C bond; at least one of the radicals $R^2$, $R^3$ and $R^6$ being other than hydrogen, possess valuable pharmacological properties, e.g., lower lipid levels and are anti-thrombotic.

4 Claims, No Drawings

LIPID LOWERING AND ANTI-THROMBOTIC 6-ARYLPYRIDAZIN-3-ONES AND A PROCESS FOR THEIR PREPARATION

BACKGROUND OF THE INVENTION

The present invention relates to 6-arylpyridazin-3-ones having pharmacological properties and to a process for the preparation thereof.

SUMMARY OF THE INVENTION

It is an object of an aspect of this invention to provide novel compounds having valuable properties, especially compounds which can be used for the preparation of medicaments.

Upon further study of the specification and appended claims, further objects and advantages of this invention will become apparent to those skilled in the art.

These objects have been attained by this invention by providing novel 6-arylpyridazin-3-ones of Formula I

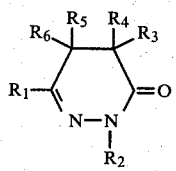

wherein $R^1$ is 4-biphenylyl or 4-phenoxyphenyl, both of which may be unsubstituted or substituted in the 4'-position by F, Cl, Br or I; $R^2$ is H, alkyl or hydroxyalkyl, each of 1–4 carbon atoms, or pyridyl; $R^3$ and $R^6$ are each H or alkyl of 1–4 carbon atoms, or together are —(CH$_2$)$_4$—; and $R^4$ and $R^5$ are each H or together are a C—C bond; but at least one of the radicals $R^2$, $R^3$ and $R^6$ is other than hydrogen.

DETAILED DISCUSSION

In Formula I, $R^1$ is preferably 4-biphenylyl, 4'-fluoro-4-biphenylyl or 4-p-chlorophenoxyphenyl, and also preferably 4'-chloro-4-biphenylyl, 4'-bromo-4-biphenylyl, p-phenoxyphenyl, 4-p-fluorophenoxyphenyl or 4-p-bromophenoxyphenyl. For $R^2$, $R^3$ and $R^6$, the alkyl group is preferably methyl, but also can be ethyl, propyl, isopropyl, butyl, sec-butyl, isobutyl or tert-butyl. For $R^2$, hydroxyalkyl is preferably 2-hydroxyethyl, but also can be, for example, 1-hydroxyethyl, 1-, 2- or 3-hydroxypropyl or 1-, 2-, 3- or 4-hydroxybutyl. Pyridyl is preferably pyrid-2-yl, but also can be pyrid-3-yl or pyrid-4-yl.

More specifically, $R^2$ is preferably H, methyl, 2-hydroxyethyl or pyrid-2-yl. $R^3$ and $R^6$ are preferably each H or methyl or together are —(CH$_2$)$_4$—. $R^4$ and $R^5$ are preferably each H.

One of the radicals $R^2$, $R^3$ and $R^6$ must be other than hydrogen. Furthermore, those compounds of Formula I in which one or two of these radicals are hydrogen are preferred.

Accordingly, the invention particularly relates to those compounds of Formula I in which at least one of the defined radicals has one of the preferred meanings given above.

In another aspect, the invention further relates to a process for the preparation of the 6-arylpyridazin-3-ones of Formula I, which comprises:

(a) reacting a carboxylic acid of Formula II $$R^1-CO-CR^5R^6-CR^3R^4-COOH \quad (II)$$

wherein $R^1$ and $R^3$ to $R^6$ are as defined for Formula I, or a reactive derivative of the carboxylic acid with a hydrazine of Formula III $$H_2N-NH-R^2 \quad (III)$$

wherein $R^2$ is as defined for Formula I; or, optionally, (b) introducing a double bond into the 4(5)-position of a resulting tetrahydro-pyridazinone of Formula I (wherein $R^4=R^5=H$) by treating it with a dehydrogenating agent.

In other respects, the preparation of the compounds of Formula I is carried out in accordance with procedures known per se, as described in the literature (for example, in the standard works such as Houben-Weyl, Methoden der Organischen Chemie (Methods of Organic Chemistry), Georg-Thieme-Verlag, Stuttgart), and under reaction conditions which are also well-known, and suitable, for these reactions. In these reactions, variants which are known per se but are not mentioned in more detail herein may also be utilized.

Some of the starting materials of Formulae II and III are known. The keto-acids of Formula II can be prepared in accordance with methods known per se, for example, by reacting biphenyls or diphenyl ethers of the formula $R^1$—H with anhydrides of dicarboxylic acids of the formula HOOC—CR$^5$R$^6$—CR$^3$R$^4$—COOH by the Friedel-Crafts method in the presence of AlCl$_3$.

Instead of the carboxylic acids of Formula II, reactive derivatives thereof may also be employed in the reaction of this invention. Particularly suitable derivatives include esters, for example, the alkyl esters, wherein the alkyl group preferably is of 1–4 carbon atoms, especially the methyl esters and ethyl esters. Additionally, it is possible to use, for example, the acid halides of the acids of Formula II, for example, the acid chlorides or acid bromides. Other suitable reactive derivatives of the carboxylic acids of Formula II can be conventionally formed in situ during the reaction, without being isolated. These include, for example, the hydrazones of the formula $R^1$—C(=N—NHR$^2$)—CR$^5$R$^6$—CR$^3$R$^4$—COOH, the hydrazides of the formula $R^1$—CO—CR$^5$R$^6$—CR$^3$R$^4$—CO—NH—NHR$^2$ and the hydrazones of these hydrazides, of the formula $R^1$—C(=N—NHR$^2$)—CR$^5$R$^6$—CR$^3$R$^4$—CO—NH—NHR$^2$.

The other starting materials can, if desired, also be formed in situ, so that they are not isolated from the reaction mixture and instead are directly reacted further to produce the compounds of Formula I.

For the reaction with the carboxylic acids of Formula II, it is advantageous to use an excess of the hydrazine derivative of Formula III, which excess can at the same time serve as the solvent. However, it is more advantageous to utilize an additional inert solvent. Preferred suitable inert solvents include alcohols, e.g., methanol, ethanol, isopropanol, n-butanol, isoamyl alcohol; glycols and their ethers, e.g., ethylene glycol, diethylene glycol, ethylene glycol monomethyl ether and ethylene glycol monoethyl ether (methylglycol and ethylglycol); as well as ethers, especially water-soluble ethers, e.g., tetrahydrofuran, dioxane or ethylene glycol dimethyl ether (diglyme); and also water; and mixtures of these solvents with one another, especially mixtures with water, for example, aqueous ethanol. The reaction temperatures are advantageously approximately 20°-approximately 200° C., preferably 60°-100° C., and the reaction times are approximately 1-48 hours. The reaction temperatures and reaction times essentially depend on the nature of the hydrazine of Formula III which is employed. If hydrazine itself (III, $R_2=H$) or its hydrate is used, heating for from one to three hours at 60°-80° C. suffices. On the other hand, when using substituted hydrazines, higher temperatures and/or longer reaction times are generally necessary.

If desired, a resulting tetrahydropyridazinone of Formula I ($R^4=R^5=H$) can be converted by dehydrogenation into the corresponding dihydropyridazinone of Formula I (wherein $R^4$ and $R^5$ together are a C—C bond).

The dehydrogenation is advantageously carried out by treatment with bromine, preferably using a carboxylic acid, e.g., acetic acid, as the solvent and carrying out the process at an elevated temperature (about 40° to 120° C.). The bromination product first formed (presumably corresponding to Formula I, but with Br in place of $R^4$ or $R^5$) is not isolated; instead, the selected reaction conditions suffice to cause its dehydrobromination to the desired dihydropyridazinone.

The compounds of Formula I can possess one or more centers of asymmetry. They can therefore be obtained from their process of preparation as racemates, or, if optically active starting materials are used, also in an optically active form. If the compounds have two or more centers of asymmetry, they are in general obtained from the syntheses as mixtures of racemates, from which the individual racemates can be isolated in the pure form, for example, by recrystallization from inert solvents. The racemates obtained can, if desired, be separated mechanically or chemically into their optical antipodes by methods known per se.

It has been found that the compounds of Formula I combine good acceptability by the patient with valuable pharmacological properties. In particular, they exhibit an anti-arteriosclerotic effect and an effect in lowering the lipid level. Thus, they lower the cholesterol level (demonstrable in the serum of rats by the method of Levine et al, Automation in Analytical Chemistry, Technicon Symposium 1967, Mediad, N.Y., pages 25-28) and lower the level of triglycerides (demonstrable by the method of Noble and Campbell, Clin. Chem. 16 (1970), pages 166-170). Furthermore, anti-thrombotic, above all thrombocyte aggregation-inhibiting properties, are displayed. The effect on the thrombocyte function, i.e., the inhibition of aggregation, can be demonstrated on rabbits in the Born test in vitro and ex vivo (Nature, 194 (1962), pages 927-929) and in the Jacobi fiber test (Thrombos. Diathes. haemorrh. 26 (1971), pages 192-202). Furthermore, antiphlogistic, fibrinolytic, blood sugar-lowering and analgesic properties, as well as effects on the central nervous system, are found, and can be determined in accordance with conventional methods used for these activities.

The compounds of Formula I can therefore be used as medicaments in human medicine and veterinary medicine. Further, they can be used as intermediate products for the preparation of other active ingredients of medicaments.

Accordingly, in another aspect, this invention further relates to the use of the compounds of Formula I for the preparation of pharmaceutical formulations, especially by non-chemical methods. For this purpose, the compounds, together with one or more solid, liquid or semi-liquid excipients or auxiliaries, and with or without one or more additional active ingredients, can be converted into a suitable dosage form.

In another aspect, this invention further relates to agents, especially pharmaceutical formulations, which contain a compound of Formula I.

These formulations may be used as medicaments in human medicine or verterinary medicine. Appropriate excipients include organic or inorganic substances which are suitable for enteral (for example, oral) or parenteral administration or for topical application and which do not react with the novel compounds, for example, water, vegetable oils, benzyl alcohols, polyethylene glycols, glycerol triacetate, gelatine, carbohydrates, such as lactose or starch, magnesium stearate, talc and vaseline. Tablets, dragees, capsules, syrups, elixirs or drops are in particular employed for oral use, suppositories for rectal use, solutions, preferably oily or aqueous solutions, as well as suspensions, emulsions or implants, for parenteral use, and ointments, creams or powders for topical use. If the medicaments are to be administered in the form of unit amounts of powder, the packaging materials, such as paper sachets or paper capsules, are also suitable excipients. The novel compounds can also be lyophilized and the resulting lyophilizates used, for example, for the preparation of injection formulations. The formulations mentioned can be sterilized and/or contain auxiliaries, such as lubricants, preservatives, stabilizers and/or wetting agents, emulsifiers, salts for influencing the osmotic pressure, buffer substances, dyestuffs, flavorings and/or scents. They can, if desired, also contain one or more additional active ingredients, for example, one or more vitamins.

This invention, in another aspect, further relates to the use of the compounds of Formula I in the therapeutic treatment of humans or animals and in combating diseases. In particular, the compounds of Formula I are suitable for the treatment and/or prophylaxis of disease symptoms entailing increased serum lipids and increased tendency to thrombosis, of primary and secondary hyperlipoproteinaemias with or without xanthomatosis, of arteriosclerosis (coronary sclerosis, cerebral sclerosis and peripheral vascular sclerosis), and of diabetic angiopathies (diabetic retinopathy).

The substances according to this invention are as a rule administered analogously to known, commercially available lipid-lowering agents (e.g., Clofibrat), preferably in dosages of approximately 10-1,000 mg, especially 50-500 mg, per dosage unit. The daily dosage is preferably approximately 0.2-100 mg/kg of body weight. The particular dose for each individual patient depends, however, on a great diversity of conventional factors, for example, on the activity of the special compound employed, on the age, body weight, general condition of health and sex of the subject, on the cost, on the time and method of administration, on the rate of excretion, on the combination of medicaments administered and on the severity of the particular disease for which the therapy is intended. Oral administration is preferred.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

Each of the compounds of Formula I mentioned in the examples which follow is particularly suitable for the preparation of pharmaceutical formulations.

EXAMPLE 1

(a) 28.6 g of 4-(4'fluoro-4-biphenylyl)-4-oxo-3-methylbutyric acid is dissolved in 430 ml of ethanol; 9 ml of 80% hydrazine hydrate is added and the mixture is boiled for 3 hours. It is then cooled and the 5-methyl-6-(4'-fluoro-4-biphenylyl)-2,3,4,5-tetrahydropyridazin-3-one which has precipitated is filtered off and washed with a small amount of acetone. m.p. 198°–199°.

(b) 18 g of bromine is added dropwise, with stirring, to a solution of 28.2 g of 5-methyl-6-(4'-fluoro-4-biphenyl-yl)-2,3,4,5-tetrahydropyridazin-3-one in 500 ml of acetic acid at 100°; the mixture is then heated for an additional 15 minutes at 100°, cooled and filtered. 5-Methyl-6-(4'-fluoro-4-biphenylyl)-2,3-dihydropyridazin-3-one is obtained. m.p. 245°–247°.

EXAMPLES 2 to 96

Analogously to Example 1, reaction of the corresponding 4-oxocarboxylic acids with the corresponding hydrazines gives the following:

2. 2-Methyl-6-p-biphenylyl-2,3,4,5-tetrahydropyridazin-3-one, m.p. 220°–221°.
3. 2-(2-Hydroxyethyl)-6-p-biphenylyl-2,3,4,5-tetrahydropyridazin-3-one, m.p. 171.5°–172.5°.
4. 4-Methyl-6-p-biphenylyl-2,3,4,5-tetrahydropyridazin-3-one.
5. 5-Methyl-6-p-biphenylyl-2,3,4,5-tetrahydropyridazin-3-one, m.p. 212°.
6. 2-Methyl-6-p-biphenylyl-2,3-dihydropyridazin-3-one.
7. 2-(2-Hydroxyethyl)-6-p-biphenylyl-2,3-dihydropyridazin-3-one.
8. 4-Methyl-6-p-biphenylyl-2,3-dihydropyridazin-3-one.
9. 5-Methyl-6-p-biphenylyl-2,3-dihydropyridazin-3-one.
10. 2-Methyl-6-(4'-fluoro-4-biphenylyl)-2,3,4,5-tetrahydropyridazin-3-one, m.p. 165°–166°.
11. 2,4-Dimethyl-6-(4'-fluoro-4-biphenylyl)-2,3,4,5-tetrahydropyridazin-3-one, m.p. 135°–136°.
12. 2,5-Dimethyl-6-(4'-fluoro-4-biphenylyl)-2,3,4,5-tetrahydropyridazin-3-one, m.p. 152.5°–153.5°.
13. 2-Ethyl-6-(4'-fluoro-4-biphenylyl)-2,3,4,5-tetrahydropyridazin-3-one.
14. 2-Ethyl-5-methyl-6-(4'-fluoro-4-biphenylyl)-2,3,4,5-tetrahydropyridazin-3-one, m.p. 128°–129°.
15. 2-Isopropyl-6-(4'-fluoro-4-biphenylyl)-2,3,4,5-tetrahydropyridazin-3-one.
16. 2-Isopropyl-5-methyl-6-(4'-fluoro-4-biphenylyl)-2,3,4,5-tetrahydropyridazin-3-one, m.p. 85°–86°.
17. 2-n-Butyl-6-(4'-fluoro-4-biphenylyl)-2,3,4,5-tetrahydropyridazin-3-one.
18. 2-n-Butyl-5-methyl-6-(4'-fluoro-4-biphenylyl)-2,3,4,5-tetrahydropyridazin-3-one, m.p. 81°–83°.
19. 2-(2-Hydroxyethyl)-6-(4'-fluoro-4-biphenylyl)-2,3,4,5-tetrahydropyridazin-3-one, m.p. 141°–142°.
20. 2-(2-Hydroxyethyl)-5-methyl-6-(4'-fluoro-4-biphenylyl)-2,3,4,5-tetrahydropyridazin-3-one, m.p. 147°–149°.
21. 2-(4-Hydroxybutyl)-6-(4'-fluoro-4-biphenylyl)-2,3,4,5-tetrahydropyridazin-3-one.
22. 2-(2-Pyridyl)-6-(4'-fluoro-4-biphenylyl)-2,3,4,5-tetrahydropyridazin-3-one.
23. 2-(3-Pyridyl)-6-(4'-fluoro-4-biphenylyl)-2,3,4,5-tetrahydropyridazin-3-one.
24. 2-(4-Pyridyl)-6-(4'-fluoro-4-biphenylyl)-2,3,4,5-tetrahydropyridazin-3-one.
25. 2-(2-Pyridyl)-5-methyl-6-(4'-fluoro-4-biphenylyl)-2,3,4,5-tetrahydropyridazin-3-one, decomposition at 205°.
26. 4-Methyl-6-(4'-fluoro-4-biphenylyl)-2,3,4,5-tetrahydropyridazin-3-one, m.p. 190°–192°.
27. 2-Methyl-6-(4'-fluoro-4-biphenylyl)-2,3-dihydropyridazin-3-one.
28. 2,4-Dimethyl-6-(4'-fluoro-4-biphenylyl)-2,3-dihydropyridazin-3-one.
29. 2,5-Dimethyl-6-(4'-fluoro-4-biphenylyl)-2,3-dihydropyridazin-3-one, m.p. 211°–213°.
30. 2-Ethyl-6-(4'-fluoro-4-biphenylyl)-2,3-dihydropyridazin-3-one.
31. 2-Ethyl-5-methyl-6-(4'-fluoro-4-biphenylyl)-2,3-dihydropyridazin-3-one.
32. 2-Isopropyl-6-(4'-fluoro-4-biphenylyl)-2,3-dihydropyridazin-3-one.
33. 2-Isopropyl-5-methyl-6-(4'-fluoro-4-biphenylyl)-2,3-dihydropyridazin-3-one.
34. 2-n-Butyl-6-(4'-fluoro-4-biphenylyl)-2,3-dihydropyridazin-3-one.
35. 2-n-Butyl-5-methyl-6-(4'-fluoro-4-biphenylyl)-2,3-dihydropyridazin-3-one.
36. 2-(2-Hydroxyethyl)-6-(4'-fluoro-4-biphenylyl)-2,3-dihydropyridazin-3-one.
37. 2-(2-Hydroxyethyl)-5-methyl-6-(4'-fluoro-4-biphenylyl)-2,3-dihydropyridazin-3-one, m.p. 176°–178°.
38. 2-(4-Hydroxybutyl)-6-(4'-fluoro-4-biphenylyl)-2,3-dihydropyridazin-3-one.
39. 2-(2-Pyridyl)-6-(4'-fluoro-4-biphenylyl)-2,3-dihydropyridazin-3-one.
40. 2-(3-Pyridyl)-6-(4'-fluoro-4-biphenylyl)-2,3-dihydropyridazin-3-one.
41. 2-(4-Pyridyl)-6-(4'-fluoro-4-biphenylyl)-2,3-dihydropyridazin-3-one.
42. 2-(2-Pyridyl)-4-methyl-6-(4'-fluoro-4-biphenylyl)-2,3,4,5-tetrahydropyridazin-3-one, m.p. 190°–191°.
43. 4-Methyl-6-(4'-fluoro-4-biphenylyl)-2,3-dihydropyridazin-3-one, m.p. 247°–248°.
44. 5-Methyl-6-(4'-fluoro-4-biphenylyl)-2,3-dihydropyridazin-3-one, m.p. 245°–247°.
45. 4-(4'-Fluoro-4-biphenylyl)-1,2,4a,5,6,7,8,8a-octahydrophthalazin-1-one, m.p. 184°–186°.
46. 4-(4'-Fluoro-4-biphenylyl)-1,2,5,6,7,8-hexahydrophthalazin-1-one, does not melt below 250°.
47. 2-Methyl-6-(4'-chloro-4-biphenylyl)-2,3,4,5-tetrahydropyridazin-3-one.
48. 4-Methyl-6-(4'-chloro-4-biphenylyl)-2,3,4,5-tetrahydropyridazin-3-one.
49. 5-Methyl-6-(4'-chloro-4-biphenylyl)-2,3,4,5-tetrahydropyridazin-3-one.
50. 2-Methyl-6-(4'-chloro-4-biphenylyl)-2,3-dihydropyridazin-3-one.
51. 4-Methyl-6-(4'-chloro-4-biphenylyl)-2,3-dihydropyridazin-3-one.
52. 5-Methyl-6-(4'-chloro-4-biphenylyl)-2,3-dihydropyridazin-3-one.
53. 4-(4'-Chloro-4-biphenylyl)-1,2,4a,5,6,7,8,8a-octahydrophthalazin-1-one, m.p. 236°–237°.
54. 4-(4'-Chloro-4-biphenylyl)-1,2,5,6,7,8-hexahydrophthalazin-1-one, does not melt below 260°.
55. 2-Methyl-6-(4'-bromo-4-biphenylyl)-2,3,4,5-tetrahydropyridazin-3-one.
56. 4-Methyl-6-(4'-bromo-4-biphenylyl)-2,3,4,5-tetrahydropyridazin-3-one.

57. 5-Methyl-6-(4'-bromo-4-biphenyl)-2,3,4,5-tetrahydropyridazin-3-one.
58. 2-Methyl-6-(4'-bromo-4-biphenylyl)-2,3-dihydropyridazin-3-one.
59. 4-Methyl-6-(4'-bromo-4-biphenylyl)-2,3-dihydropyridazin-3-one.
60. 5-Methyl-6-(4'-bromo-4-biphenylyl)-2,3-dihydropyridazin-3-one.
61. 5-Methyl-6-(4'-iodo-4-biphenylyl)-2,3,4,5-tetrahydropyridazin-3-one.
62. 5-Methyl-6-(4'-iodo-4-biphenylyl)-2,3-dihydropyridazin-3-one.
63. 2-Methyl-6-p-phenoxy-phenyl-2,3,4,5-tetrahydropyridazin-3-one.
64. 2-Methyl-6-p-phenoxy-phenyl-2,3-dihydropyridazin-3-one.
65. 2-Methyl-6-(4-p-fluorophenoxy-phenyl)-2,3,4,5-tetrahydropyridazin-3-one.
66. 2-(2-Hydroxyethyl)-6-(4-p-fluorophenoxy-phenyl)-2,3,4,5-tetrahydropyridazin-3-one.
67. 2-(2-Pyridyl)-6-(4-p-fluorophenoxy-phenyl)-2,3,4,5-tetrahydropyridazin-3-one.
68. 4-Methyl-6-(4-p-fluorophenoxy-phenyl)-2,3,4,5-tetrahydropyridazin-3-one.
69. 5-Methyl-6-(4-p-fluorophenoxy-phenyl)-2,3,4,5-tetrahydropyridazin-3-one.
70. 2-Methyl-6-(4-p-fluorophenoxy-phenyl)-2,3-dihydropyridazin-3-one.
71. 2-(2-Hydroxyethyl)-6-(4-p-fluorophenoxy-phenyl)-2,3-dihydropyridazin-3-one.
72. 2-(2-Pyridyl)-6-(4-p-fluorophenoxy-phenyl)-2,3-dihydropyridazin-3-one.
73. 4-Methyl-6-(4-p-fluorophenoxy-phenyl)-2,3-dihydropyridazin-3-one.
74. 5-Methyl-6-(4-p-fluorophenoxy-phenyl)-2,3-dihydropyridazin-3-one.
75. 2-Methyl-6-(4-p-chlorophenoxy-phenyl)-2,3,4,5-tetrahydropyridazin-3-one, m.p. 131°–133°.
76. 2,4-Dimethyl-6-(4-p-chlorophenoxy-phenyl)-2,3,4,5-tetrahydropyridazin-3-one, m.p. 88°–90°.
77. 2-(2-Hydroxyethyl)-6-(4-p-chlorophenoxy-phenyl)-2,3,4,5-tetrahydropyridazin-3-one, m.p. 132°–133°.
78. 2-(2-Hydroxyethyl)-4-methyl-6-(4-p-chlorophenoxy-phenyl)-2,3,4,5-tetrahydropyridazin-3-one, m.p. 112°–113°.
79. 4-Methyl-6-(4-p-chlorophenoxy-phenyl)-2,3,4,5-tetrahydropyridazin-3-one, m.p. 129°–130°.
80. 5-Methyl-6-(4-p-chlorophenoxy-phenyl)-2,3,4,5-tetrahydropyridazin-3-one, m.p. 179°–180°.
81. 2-Methyl-6-(4-p-chlorophenoxy-phenyl)-2,3-dihydropyridazin-3-one.
82. 2,4-Dimethyl-6-(4-p-chlorophenoxy-phenyl)-2,3-dihydropyridazin-3-one.
83. 2-(2-Hydroxyethyl)-6-(4-p-chlorophenoxy-phenyl)-2,3-dihydropyridazin-3-one.
84. 2-(2-Hydroxyethyl)-4-methyl-6-(4-p-chlorophenoxy-phenyl)-2,3-dihydropyridazin-3-one.
85. 4-Methyl-6-(4-p-chlorophenoxy-phenyl)-2,3-dihydropyridazin-3-one.
86. 5-Methyl-6-(4-p-chlorophenoxy-phenyl)-2,3-dihydropyridazin-3-one.
87. 4-(4-p-Chlorophenoxy-phenyl)-1,2,4a,5,6,7,8,8a-octahydrophthalazin-1-one.
88. 4-(4-p-Chlorophenoxy-phenyl)-1,2,5,6,7,8-hexahydrophthalazin-1-one.
89. 2-Methyl-6-(4-p-bromophenoxy-phenyl)-2,3,4,5-tetrahydropyridazin-3-one.
90. 4-Methyl-6-(4-p-bromophenoxy-phenyl)-2,3,4,5-tetrahydropyridazin-3-one, m.p. 156°–157°.
91. 5-Methyl-6-(4-p-bromophenoxy-phenyl)-2,3,4,5-tetrahydropyridazin-3-one.
92. 2-Methyl-6-(4-p-bromophenoxy-phenyl)-2,3-dihydropyridazin-3-one.
93. 4-Methyl-6-(4-p-bromophenoxy-phenyl)-2,3-dihydropyridazin-3-one, m.p. 218°–219°.
94. 5-Methyl-6-(4-p-bromophenoxy-phenyl)-2,3-dihydropyridazin-3-one.
95. 4-(4-p-Bromophenoxy-phenyl)-1,2,4a,5,6,7,8,8a-octahydrophthalazin-1-one.
96. 4-(4-p-Bromophenoxy-phenyl)-1,2,5,6,7,8-hexahydrophthalazin-1-one.

EXAMPLE 97

A mixture of 31.2 g of 2-methyl-4-(4'-fluoro-4-biphenylyl)-4-oxo-2-butenoic acid ethyl ester, 60 ml of 24% aqueous hydrazine hydrate solution and 50 ml of water is boiled for one hour. When it has cooled, 25 ml of concentrated hydrochloric acid is added and the liquid is boiled for an additional 30 minutes. After again cooling the mixture, the 4-methyl-6-(4'-fluoro-4-biphenylyl)-2,3-dihydropyridazin-3-one obtained is filtered off and washed with water. m.p. 247°–248°.

EXAMPLE 98

28.4 g of 2-methyl-4-(4'-fluoro-4-biphenylyl)-4-oxo-2-butenoic acid is dissolved in 100 ml of methanol; 15.4 g of $K_2CO_3$ is added and the mixture is stirred for 6 hours at 20°. It is then acidified with hydrochloric acid, 5.4 ml of hydrazine hydrate is added and the batch is boiled for 2 hours. Thereafter, it is again acidified; the solution is concentrated and cooled; and the 4-methyl-6-(4'-fluoro-4-biphenylyl)-2,3-dihydropyridazin-3-one obtained is filtered off and washed with water. m.p. 247°–248°.

The examples which follow relate to pharmaceutical formulations which contain compounds of Formula I.

EXAMPLE A: Tablets

A mixture of 1 kg of 4-methyl-6-(4'-fluoro-4-biphenylyl)-2,3-dihydropyridazin-3-one, 4 kg of lactose, 1.2 kg of potato starch, 0.2 kg of talc and 0.1 kg of magnesium stearate is conventionally pressed to form tablets, each containing 10 mg of active ingredient.

EXAMPLE B: Dragees

Tablets are pressed analogously to Example A and are subsequently coated in the conventional manner with a coating of sucrose, potato starch, talc, tragacanth and dyestuff.

EXAMPLE C: Capsules 2 kg of 5-methyl-6-(4'-fluoro-4-biphenylyl)-2,3,4,5-tetrahydropyridazin-3-one is filled in the conventional manner into hard gelatine capsules, so that each capsule contains 20 mg of active ingredient.

Tablets, dragees and capsules which contain one or more of the other active ingredients of Formula I may be obtained analogously.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. 5-Methyl-6-p-biphenylyl-2,3,4,5-tetrahydropyridazin-3-one.

2. A pharmaceutical composition comprising an amount of a compound of claim 1 effective to lower the lipid level in a patient and a pharmaceutically acceptable adjuvant.

3. The pharmaceutical composition of claim 2, wherein the amount of the active ingredient is 10–1,000 mg.

4. A method of lowering the lipid level in a patient which comprises administering to the patient an amount of a compound of claim 1 effective to lower the lipid level.

* * * * *